United States Patent [19]
Kasper

[11] Patent Number: 5,985,544
[45] Date of Patent: Nov. 16, 1999

[54] PRIMERS AND PROBES FOR THE DETECTION OF HIV

[75] Inventor: Pia Kasper, Obereglfing, Germany

[73] Assignee: Roche Diagnostics GmbH, Mannheim, Germany

[21] Appl. No.: 08/957,156

[22] Filed: Oct. 24, 1997

[30] Foreign Application Priority Data

Oct. 24, 1996 [DE] Germany .......................... 196 44 248

[51] Int. Cl.$^6$ .............................. C12Q 1/68; C12P 19/34; C07H 21/04; C07H 21/02
[52] U.S. Cl. .................................. 435/5; 435/6; 435/91.2; 536/24.3; 536/24.33; 935/77; 935/78
[58] Field of Search .................................. 435/6, 5, 91.2; 536/24.3, 24.33; 935/77, 78

[56] References Cited

U.S. PATENT DOCUMENTS 5,759,770  6/1998  Guertler et al. ............................ 435/5

FOREIGN PATENT DOCUMENTS 0 403 333 A2  12/1990  European Pat. Off. .
0 617 132 A2  9/1994  European Pat. Off. .

OTHER PUBLICATIONS

Human Retroviruses and AIDS 1994, I–A–1, Los Alamos National Laboratory, Los Alamos, New Mexico 87545, USA, Editor G. Myers et al.

*Primary Examiner*—Stephanie Zitomer
*Attorney, Agent, or Firm*—Nikaido, Marmelstein, Murray & Oram LLP

[57] ABSTRACT

Using oligonucleotides selected from the 3'-terminal region of the gag-gene of HIV-1 there can be detected much more subtypes than using the known oligonucleotides. This improves reliability of the HIV-1 determination.

13 Claims, No Drawings

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 607 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

```
CTATAAAACT CTAAGAGCCG AGCAAGCTTC ACAGGATGTA AAAAATTGGA TGACAGAAAC      60

CTTCCTGGTC CAAAATGCGA ACCCAGATTG TAAAACTATT TTAAAAGCAT TGGGACCAGC     120
```

```
AGCTACACTA GAAGAAATGA TGACAGCATG TCAGGGAGTA GGGGGACCCA GCCATAAAGC      180

AAGAATTTTG GCTGAAGCAA TGAGCCAAGT AACAAATTCA GCTACCATAA TGCTGCAGAA      240

AGGTAATTTT AGGGACCAAA GAAAAATTGT TAAGTGTTTC AACTGTGGCA AAGTAGGGCA      300

CATAGCCAAA AATTGCAGGG CCCCTAGGAA AAAGGGCTGT TGGAAATGTG GAAAGGAAGG      360

ACACCAAATG AAAGATTGCA CTAATGAGGG ACGACAGGCT AATTTTTTAG GGAAAATCTG      420

GCCTTCCCAC AAGGGAAGGC CAGGGAACTT TCTTCAGAGC AGACCAGAGC CAACAGCCCC      480

ACCAGAAGAG AGCTTCAGGT TTGGGGAAGA GACAACTCCC TCTCAGAAGC AGGAGAAGAT      540

AGACAAGGAA CTGTATCCTT TAGCTTCCCT CAAATCACTC TTTGGCAACG ACCCATCGTC      600

ACAGTAA                                                               607

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 2:

TGATGACAGC ATGTCAGGGA GTGG                                            24

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 3:

TCCACATTTC CAACACCCCT TTTT                                            24

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

TTCAATTGTG GCAAAGAAGG G                                               21

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

AAAGCAAGAA TTTTGGCTGA AG                                              22
```

PRIMERS AND PROBES FOR THE DETECTION OF HIV

This application claims priority under 35 U.S.C. 119 (a)–(d) of application No. DE 196 44 248,6 filed Oct. 24, 1996.

Subject matter of the invention are oligonucleotide, especially primers and probes, for the detection of HIV; further, a method for detecting HIV using these primers and probes.

The detection of the human immunodeficiency virus (HIV) is one of the greatest challenges of analytical diagnostics. Numerous methods are already available for this procedure, which are based either on the immunological detection of HIV antigens or HIV-induced antibodies, intrinsic HIV enzymes, e.g. intrinsic HIV reverse transcriptase, or HIV-specific nucleic acids. Since the causative agent and, therefore, the nucleic acids associated with it are present in human bodily fluids in very small concentrations, the sensitivity of a detection method is a decisive factor for its usability. The polymerase chain reaction (PCR), as described in EP-B-0 200 362 and EP-B-0 201 184, for instance, is the most sensitive method at this time for the direct detection of HIV. Using the PCR, important information on the course of the disease and therapy monitoring can be obtained from blood samples from infected persons. Detection methods that are not based on the amplification of parts of HIV nucleic acids or that include a single hybridization of a probe with which the HIV nucleic acid is detected are not as sensitive as the PCR.

Since the discovery of HIV-1, it was determined that the nucleic acid sequences of HIV-1 having different origins are different from each other. The different types of HIV-1 are usually called subtypes. At least nine subtypes are known at this time, identified as subtypes A through H and O (e.g. Human Retroviruses and AIDS, Los Alamos Natl. Laboratory, Los Alamos, N.Mex. 1994; ed. G. Myers et all, I-A-1). The methods described so far are not capable of detecting five or more of these subtypes, and especially not the subtypes A and G in conjunction with other subtypes.

The task of the present invention, therefore, was to provide reagents and methods with which more subtypes can be detected than was previously possible.

Subject matter of the invention, therefore, is an HIV-1-specific oligonucleotide, characterized in that its sequence is selected from the series of nucleotide positions from 900 to the 3' end of the gag gene of HIV-1.

An oligonucleotide is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction is made between oligodeoxyribonucleotides that do not have a hydroxyl group in the 2' unit, and oligoribonucleotides that have a hydroxyl group in this position. The oligoribonucleotides also include compounds, however, in which the hydrogen of the hydroxyl group is replaced with organic groups, e.g. an allyl group. Compounds of this nature have been known to the expert for quite some time. Recently, molecules were also described in which the sugar phosphate backbone of normal oligonucleotides is replaced with a peptide backbone. An especially preferred group of compounds of this nature is described in WO 92/20702; they are called PNA. Both these compounds and oligonucleotides have bases on the backbone that are capable of forming hydrogen bridge compounds with complementary bases. These bases include the natural bases A, G, C, T and U, as well as artificial bases such as Deaza G.

The oligonucleotides in accordance with the invention are preferably between 10 and 100 bases long. The homology or complementarity of consecutive bases of at least 10 to 30 of these bases is 80%, preferably 90%, and particularly preferred 100% with the series of nucleotide positions described above. The remaining bases (e.g. on one or both ends of the sequence), if available, can have a sequence that is so dissimilar to either HIV-1 or other nucleic acids contained in a sample to be tested as usual for HIV-1 that hybridization cannot take place. It is especially preferred for the HIV-1-specific region of the oligonucleotide of this invention to be between 13 and 25 nucleotides long.

A first sequence is described as being 100% complementary with a second nucleotide sequence in terms of this invention when its consecutive bases follow the Watson-Crick rule of consecutive bases of the second nucleotide sequence. Substitutions are allowed in this case, however, in which bases—especially artificial bases—are used in place of the natural bases that have a specific interaction that is similar to that of the base that is complementary to the substituted base. Homologous to a second sequence as understood in this invention refers to a consecutive initial sequence of bases that is just as complementary to a third nucleic acid with consecutive bases as the second nucleotide sequence of consecutive bases of the same length.

Nucleic acids of HIV-1 refers to genomic RNA of viruses that belong to the HIV viruses. A distinction is made at this time between subtypes A through H and O of HIV-1. The complement of these nucleic acids refers to the complementary sequence.

A primer refers to an oligonucleotide that can be extended with a DNA polymerase using monodeoxyribonucleoside triphosphates and a nucleic acid that is used as a matrix. This primer preferably has a 3'-hydroxyl group on an end that is facing the 5' end of the matrix nucleic acid when it is hybridized with the matrix.

A set of primers refers to a combination or mixture of at least two types of primers, the first primer of which can be extended using the matrix nucleic acid while forming an extension product in such a way that the second primer can hybridize with this extension product in a region of the extension product that lies in the 3' direction of the extendable end of the first primer, and that the extendable end of the second primer points in the 5' direction of the extension product of the first primer. The primers that are suitable for performing the polymerase chain reaction (PCR) and that meet this definition are described in EP-B-0 201 184.

Amplification of nucleic acids refers to the amplification of nucleic acids or subregions of these nucleic acids. One can preferably amplify parts of nucleic acids between 100 and 300 bases long by selecting the proper primer sequences and using the PCR, for instance.

The term amplification is also meant to include transcription of RNA into DNA.

The gag gene of HIV-1 refers to the gene that codes for p24 (capside protein), p17 (matrix protein) and p6, for instance. This gene includes conserved and relatively variable sequence regions. A core of the present invention is the use of sequences that are either complementary or homologous to a consecutive sequence of bases within the range of nucleotide positions from 900 to the 3' end of this gene. Especially preferred is the series of nucleotide positions from 900 to the 3' end of the gag gene of HIV-1, subtype B, strain HIV-RF (SEQ.ID.NO. 1, Human Retroviruses and AIDS 1994, I-A-1, Los Alamos National Laboratory, Los Alamos, N.Mex. 87545, USA, Editor G. Myers et al.).

HIV-1 specificity refers to the characteristic that the pertinent nucleotide sequence—except in HIV-1—is not present in nucleic acids that are contained in samples that are tested as usual for the presence of HIV-1. It is especially preferred for the pertinent sequence to be completely unique, i.e. it is not found in other samples, either. Specific amplification or specific detection refers to a method in which only H-1 is amplified or detected, but not other organisms or nucleic acids that may be present in the sample. HIV-1 specificity of a sequence as understood in the present invention, however, also means that the sequence is so non-specific that at least 5 subtypes of HIV-1 can be identified, amplified and detected.

Oligonucleotides in accordance with the invention can be identified using a special, preferred method in the range of positions described. This method is based on the pertinent sequence of a strain of a subtype of HIV-1, preferably subtype B, and especially preferred from the strain RF. In this method, partial sequences of 20 to 30 bases in length having a GC content between 50 and 60%, no self-complementarity on the 3' end, and no CG run on the 3' end or any palindromes are searched for in this sequence, preferably using a computer program. The consensus sequence of the subtype belonging to this sequence of the strain is determined, for instance, using the book "Human Retroviruses and AIDS", 1994, described above. The consensus sequence is the sequence that contains the most prevalent base in all strains in the certain position. Only those consensus sequences were processed further that have no more than 2 mismatches with the consensus sequences of the same positions of the remaining subtypes, preferably subtypes A and C through H. If these sequences have mismatches with one of the strains on their 3' ends, these nucleotides (1 to 2 nucleotides away from the end) will not be included in these sequences.

In selecting the primer sequences, the oligonucleotide sequences found in this manner are combined into sets of 2 primers each with different sequences in such a way that the 5' ends of the primers are positioned between 150 and 400 bases away from each other.

Especially preferred primer sets are those in which another HIV-1-specific sequence lies within this range. Most preferably, this sequence can be used as a probe for the detection of amplificates.

Using this method, the following sequences were found to be especially preferred oligonucleotides:

```
GAG1037:  TGATGACAGCATGTCAGGGAGTGG   SEQ. ID. NO. 2

GAG1228:  TCCACATTTCCAACACCCCTTTTT   SEQ. ID. NO. 3

GAG1177:  TTCAATTGTGGCAAAGAAGGG      SEQ. ID. NO. 4

GAG1075:  AAAGCAAGAATTTTGGCTGAAG     SEQ. ID. NO. 5
```

The combination GAG1037/1228 has proven to be especially preferred as a primer pair. Of the probe oligonucleotides, GAG1177 has proven to be especially preferable.

The oligonucleotides of the invention can be manufactured using known methods, e.g. solid phase synthesis with phosphoramidites. Suitable automated synthesis devices are available for performing this procedure.

The oligonucleotides in accordance with the invention can be used as primers or probes. When used as a probe, it is preferable for the oligonucleotide to contain a non-HIV-specific label in addition to the HIV-specific sequence. The label can be any type of differentiating label, e.g. a nucleic acid sequence that is not HIV-specific, a detectable molecule, e.g. a fluorescent group (that can be inserted per the known methods using fluorescein isothiocyanate), or digoxigenin, as described in EP-A-0 324 474, or a molecule that can be immobilized, such as biotin (by means of which the oligonucleotide can be bound to a streptavidin-coated surface, for instance).

Subject matter of the invention, therefore, is also a set of primers for the amplification of HIV nucleic acids, characterized in that it contains at least two different oligonucleotides in accordance with the definition, above. These sets of primers can be used preferably in amplification procedures using the polymerase chain reaction or the nucleic acid sequence based amplification (NASBA) as described in EP-A-0 329 822. The expert is familiar with the basic principles of these methods.

Subject matter of the invention is also a procedure for the specific amplification of HIV-1 nucleic acids using a set of primers with which nucleic acids of at least 5 subtypes of HIV-1 are detected and amplified. It is especially preferred for subtype B to be one of the subtypes detected, especially in combination with one or more of the subtypes A, C, D, E, F and G.

Yet another subject matter of the invention is a method for the detection of HIV-1 using amplification of HIV-1 nucleic acid sequences and detection of the amplificates, whereby the amplification is performed with a primer set of the type described above. Especially preferred are detection procedures in which the amplificates formed are detected using a nucleic acid probe that fits the definition of oligonucleotides, above, and that binds within the primer hybridization sites in the amplificate.

It is an advantage of the invention that it can be used to detect more subtypes of HIV-1 than was previously possible.

The following examples explain the present invention in greater detail:

EXAMPLE 1

A. Sample Preparation

The blood samples used were pretreated with the QIAamp HIV Kit (Qiagen Cat. No. 29504) to isolate the RNA.

B. Reverse Transcription 10 ml of the solution obtained were treated with 10 ml RT mix (composition, below) in PCR tubes in a Perkin Elmer 9600 thermal cycler (30 min at 42° C., 5 min at 94° C., cool and maintained at 4° C.):

| Reagent | Stock Solution | Volume | Final Concentration |
| --- | --- | --- | --- |
| 5 x RT buffer | 5 x | 4 ml | 1 x |
| dNTP mix | 10 mM | 0.5 ml | 250 mM |
| Hexamers | 20 nM | 1 ml | 1 mM |
| DEPC-H$_2$O |  | 3.5 ml |  |
| RNasin | 2 U/ml | 0.5 ml | 1 U |
| M.MuLV-RT | 20 U/ml | 0.5 ml | 10 U |

Legend:
dNTP mix: PCR nucleotide mix (Boehringer Mannheim GmbH, Cat. No. 1581295)
Rnasin: RNase inhibitor (Boehringer Mannheim GmbH, Cat. No. 1277081)
M.MuLV-RT, RT buffer: Reverse transcriptase (Boehringer Mannheim Cat. No. 1062603)
DEPC: Sterile, bidistilled water
Hexamers: Mixture of hexadeoxyribonucleotides having all possible sequences (Random Hexamers, Boehringer Mannheim GmbH, Cat. No. 1277081)

C. PCR 80 ml PCR mix were added to 20 ml of the mixture from the RT:

| Reagent | Stock Solution | Volume | Final Concentration |
|---|---|---|---|
| 10 x PCR | 10 x | 10 ml | 1 x |
| DIG-dNTPs | | 10 ml | |
| 5' primer | 5 mM | 4 ml | 200 nM 20 pmol/PCR |
| 3' primer | 5 mM | 4 ml | 200 nM 20 pmol/PCR |
| H₂O | | 51 ml | |
| Taq DNA Pol | 5 U/ml | 1 ml | 5 U |
| RT mixture | | 20 ml | |
| Final volume | | 100 ml | |

Legend:
10 x PCR, DIG-dNTPs: from PCR Dig Labelling Mix (Cat. No. 1585550, Boehringer Mannheim GmbH)
5' primer: e.g. SEQ. ID. NO. 2
3' primer: e.g. SEQ. ID. NO. 3
Taq DNA polymerase: (Boehringer Mannheim GmbH, Cat. No. 1146165)

The mixture was treated as follows in a Perkin Elmer thermal cycler (PE 9600):

| | | |
|---|---|---|
| | 3 min | 94° C. |
| then 40 cycles | 30 s | 94° C. |
| | 30 s | 50° C. |
| | 1 min | 72° C. |
| then at | | 4° C. |

The amplificates can be stored at 4° C. or, for longer periods of time, at −20° C.

D. Detection

The amplificates were detected using the Enzymun DNA Detection Test (Boehringer Mannheim GmbH, Cat. No. 1447777) on the ES 300 (Boehringer Mannheim GmbH).

In this procedure, an oligonucleotide whose sequence lies within the amplified region and that was biotinylated using a biotin-amidite link (ABI, Cat. No. 401396), e.g. SEQ. ID. NO. 4 or SEQ. ID. NO. 5, was used as the capture probe. The hybrids were bound to streptavidin tubes (Boehringer Mannheim GmbH) and detected with anti-DIG antibodies. For this step, the PCR product was diluted with denaturing solution in a 1:10 ratio. The concentration of the capture probe was 75 ng/ml hybridization buffer. Otherwise the procedure was performed according to the instructions provided in the package insert.

Documents EP-B-0 200 362 and EP-B-0 201 184 describing PCR methods; WO 92/20702, describing PNA molecules; and EP-A-0 329 822, describing the NASBA method, are expressly incorporated herein in their entireties.

Also contemplated for use as oligonucleotides according to the invention are those oligonucleotides capable of recognizing 5 subtypes of HIV-1 when utilized in either the PCR or NASBA methodologies, wherein the oligonucleotides are obtained from a sequence having more than 80% complementarily or 80% homology to a fragment of 10 consecutive bases of SEQ ID NO 1. More preferably, such a sequence possess at least 90–100% complementarily or homology to the 10-base fragment of SEQ ID NO 1. Such a sequence according to the invention also possesses the characteristics enumerated above, including: a GC content of between 50–60%; at a 3' end of said sequence, an absence of self-complementarity and an absence of a CG run; an absence of any palinodrome within said sequence; no more than 2 mismatches between the 10 base consecutive sequence and the corresponding consensus sequences of the same positions of HIV-1 subtypes A–C and H.

A "biological sample" from which HIV-1 may be detected according to the invention includes for example, serum, semen, mucous or other bodily exudate. HIV-1 specificity is meant to exclude from detection, for example, tissue, other viruses, nucleic acids, or contaminants which may be found in such samples used for HIV-1 testing.

Oligonucleotide homologs, "homoligos" posessing 90–100% homology to any of SEQ ID NOS 2–5, such that homology is sufficient to identify the same HIV-1 subtypes as identified by PCR or NASBA using any of SEQ ID NOS 2–5 alone or in combination, also are contemplated according to the invention. For example, a single base substitution within the sequence of any one or pair of the four oligonucleotides, so long as that resultant homoligo or homoligo pair still permits identification of at least 5 subtypes.

Further, a kit for detecting HIV-1 comprises primers according to the invention and separately packaged reagents for performing PCR. Such a kit preferably comprises at least one labelled oligonucleotide having a non-HIV-1 specific label, wherein that labelled oligonucleotide detects HIV-1 in the region amplified by the primers. The primers of the kit may be selected from the group consisting of SEQ ID NO 2, SEQ ID NO 3, SEQ ID NO 4 and SEQ ID NO 5, preferably SEQ ID NO 2 and SEQ ID NO 3. In a preferred kit, the labelled oligonucleotide consists of SEQ ID NO 4.

I claim:

1. An oligonucleotide selected from the group consisting of SEQ ID NO:3, SEQ ID NO:4, and SEQ ID NO:5.

2. A set of primers consisting of oligonucleotides of SEQ ID NO:2 and SEQ ID NO:3.

3. The oligonucleotide of claim 1, further comprising a label.

4. The oligonucleotide of claim 3, wherein the label is selected from the group consisting of a fluorescent group, digoxigenin and biotin.

5. The oligonucleotide of claim 4, wherein the sequence is SEQ ID NO:4.

6. A method for specifically detecting HIV-1 nucleic acids in a biological sample comprising:
   a) contacting said sample with a set of primers of claim 2 under conditions such that said HIV-1 nucleic acids can hybridize with said primers;
   b) reverse transcribing and amplifying said nucleic acids to obtain amplified HIV-1 nucleic acids; and
   c) detecting the presence of said amplified HIV-1 nucleic acids.

7. The method of claim 6, wherein said detecting the presence of said amplified HIV-1 nucleic acids comprises contacting said amplified HIV-1 nucleic acids with a labeled oligonucleotide to obtain labeled HIV-1 nucleic acids, and identifying said labeled nucleic acids.

8. The method of claim 7, wherein said labeled oligonucleotide comprises the sequence of SEQ ID NO:4.

9. The method of claim 6, wherein the amplifying said nucleic acids is accomplished by nucleic acid sequence based amplification (NASBA).

10. The method of claim 6, wherein the amplifying said nucleic acids is accomplished by polymerase chain reaction (PCR).

11. A kit for the detection of HIV-1, comprising the set of primers of claim 2, and separately packaged reagents for performing Polymerase Chain Reaction (PCR).

12. The kit of claim 11, further comprising at least one labeled oligonucleotide for detecting amplified HIV-1 nucleic acid.

13. The kit of claim 12, wherein the labeled oligonucleotide comprises the sequence of SEQ ID NO:4 or SEQ ID NO:5.

* * * * *